United States Patent
Popovic et al.

(10) Patent No.: US 10,414,054 B2
(45) Date of Patent: Sep. 17, 2019

(54) FORCE FEEDBACK GRIPPING DEVICE WITH MAGNETORHEOLOGICAL BASED ACTUATOR

(71) Applicant: KONINKLIJKE PHILIPS N.V., Eindhoven (NL)

(72) Inventors: Aleksandra Popovic, New York, NY (US); Sitharthan Kamalakaran, Pelham, NY (US); Douglas Allen Stanton, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/780,015

(22) PCT Filed: Mar. 25, 2014

(86) PCT No.: PCT/IB2014/060114
§ 371 (c)(1),
(2) Date: Sep. 25, 2015

(87) PCT Pub. No.: WO2014/155279
PCT Pub. Date: Oct. 2, 2014

(65) Prior Publication Data
US 2016/0031091 A1    Feb. 4, 2016

Related U.S. Application Data

(60) Provisional application No. 61/806,421, filed on Mar. 29, 2013.

(51) Int. Cl.
B25J 15/02 (2006.01)
H01F 7/20 (2006.01)
(Continued)

(52) U.S. Cl.
CPC ........... B25J 15/0246 (2013.01); A61B 17/29 (2013.01); A61B 34/30 (2016.02); H01F 7/204 (2013.01);
(Continued)

(58) Field of Classification Search
CPC .... B25J 15/0246; B25J 9/1633; B25J 13/082; A61B 17/29; A61B 2017/2932;
(Continued)

(56) References Cited

U.S. PATENT DOCUMENTS 6,400,549 B1 * 6/2002 Davis, III ................. B25J 7/00
361/144
6,408,289 B1 * 6/2002 Daum ..................... A61F 2/586
706/44

(Continued)

FOREIGN PATENT DOCUMENTS

DE    102004041690 A1    3/2005
JP         61071988 A    4/1986
(Continued)

OTHER PUBLICATIONS

"Magnetorheological Elastomers With Continually Adjustable Hardness", Fraunhof ISC, www.isc.fraunhofer.de, (no date).

(Continued)

Primary Examiner — Dean J Kramer (57) ABSTRACT

A force feedback gripping device employs a mechanical gripper (23), an electromagnetic actuator (22) and a force feedback controller (21). The mechanical gripper (23) is operable to be actuated to one of a plurality of gripping poses for gripping an object. The electromagnetic actuator (22) includes a magnetorheological elastomer ("MRE"), wherein the MRE is operable to be transitioned between a plurality of shapes dependent upon a variable strength of a magnetic field applied to the MRE, and wherein each shape (Continued)

of the MRE actuates the mechanical gripper (23) to one of the gripping poses. The force feedback controller (21) is operable to control the variable strength of the magnetic field applied to the MRE based on an estimation of a gripping force of the mechanical gripper (23) and on a sensing of a load force of the object responsive to the gripping force of the mechanical gripper (23).

17 Claims, 7 Drawing Sheets

(51) Int. Cl.
 *A61B 17/29* (2006.01)
 *A61B 34/30* (2016.01)
 *A61B 17/00* (2006.01)
 *A61B 90/00* (2016.01)
(52) U.S. Cl.
 CPC .......... *A61B 2017/00398* (2013.01); *A61B 2017/00876* (2013.01); *A61B 2090/065* (2016.02); *A61B 2562/0247* (2013.01); *A61M 2205/0288* (2013.01)
(58) Field of Classification Search
 CPC ........... A61B 2017/00398; A61B 2017/00876; A61B 2562/0247; A61B 34/30; A61B 2090/065; A61M 2205/0288; H01F 7/204
 USPC ....................................................... 294/192
 See application file for complete search history.

(56) References Cited

U.S. PATENT DOCUMENTS

| | | | |
|---|---|---|---|
| 7,113,166 B1 | 9/2006 | Rosenberg et al. | |
| 7,608,197 B2* | 10/2009 | Bose | F16F 1/361 252/62.52 |
| 8,718,813 B2* | 5/2014 | Mankame | B25J 9/1085 310/311 |
| 2002/0057152 A1 | 5/2002 | Reinhold | |
| 2011/0071670 A1* | 3/2011 | Mankame | B25J 9/1085 700/245 |
| 2011/0089708 A1* | 4/2011 | Mankame | B25J 9/1085 294/86.4 |
| 2012/0174573 A1* | 7/2012 | Skurkis | D07B 1/0673 60/527 |
| 2013/0068479 A1 | 3/2013 | Aldossary | |

FOREIGN PATENT DOCUMENTS

| | | |
|---|---|---|
| JP | 10249776 A | 9/1998 |
| WO | 2009133056 A1 | 11/2009 |
| WO | 2011003037 A1 | 1/2011 |
| WO | 2012026332 A1 | 3/2012 |
| WO | 2012102902 A1 | 8/2012 |

OTHER PUBLICATIONS

A. Pettersson et al, "Design of a magnetorheological robot gripper for handling of delicate food products with varying shapes", Journal of Food Engineering. http://www.sciencedirect.com/science/article/pii/S0260877410000130, May 24, 2012.

* cited by examiner

FORCE FEEDBACK GRIPPING DEVICE WITH MAGNETORHEOLOGICAL BASED ACTUATOR

CROSS-REFERENCE TO PRIOR APPLICATIONS

This application is the U.S. National Phase application under 35 U.S.C. § 371 of International Application No. PCT/IB2014/060114, filed on Mar. 25, 2014, which claims the benefit of U.S. Provisional Patent Application No. 61/806,421, filed on Mar. 29, 2013. These applications are hereby incorporated by reference herein.

The present invention generally relates to force feedback gripping devices, particularly for medical interventions. The present invention specifically relates to force feedback control of a magnetorheological elastomer ("MRE") in actuating a mechanical gripper for applying a gripping force upon an object, particularly an anatomical object (e.g., an organ, a blood vessel, a foreign body, etc.).

Most of the conventional grippers/tweezers used in medicine and industrial manipulation do not provide force-feedback. The lack of force controlled motion can lead to damage of a manipulated object (e.g., tissue tearing in medical applications) or damage to the gripper, which may cause inflammation if part of the gripper remains in the patient's body, or structural defect in manufacturing.

Force-feedback grippers known in art are using conventional actuation, such as electro-motors and mechanical transmission. Response time of these actuators is typically low since it depends on inertial moment of the transmission unit. Furthermore, these assemblies are difficult to be miniaturized since they are manufactured from a lot of moving parts. The same is true for pneumatic actuators.

Alternatives, such as electrothermal actuators can be miniaturized, but dissipate heat which may not be acceptable in some applications both in medicine and in manufacturing.

One form of the present invention is a magnetorheological elastomer ("MRE") gripping device employing a mechanical gripper and electromagnetic actuator. The mechanical gripper is operable to be actuated to one of a plurality of gripping poses for gripping an object. The electromagnetic actuator includes a MRE, wherein the MRE is operable to be transitioned between a plurality of shapes dependent upon a variable strength of a magnetic field applied to the MRE, and wherein each shape of the MRE actuates the mechanical gripper to one of the gripping poses.

For purposes of the present invention, a "shape" of the MRE broadly encompasses any general shape (e.g., circles, spheres, polygons, prisms, cylinders, cones, etc.), and a "plurality of shapes" of the MRE broadly encompasses (1) variances in one or more dimensions of the same general shape, and/or (2) a transition between two (2) general shapes. For example, a MRE may have a general prism shape that is in cubic form when a minimal strength of the magnetic field is applied to the MRE and that is elongated to a rectangular form when a maximal strength of the magnetic field is applied to the MRE, or vice-versa. By further example, the MRE may have a cylinder shape when a minimal strength of the magnetic field is applied to the MRE that transitions to a cone shape as the maximal strength of the magnetic field is applied to the MRE, or vice-versa.

A second form of the present invention is a force feedback gripping device employing a mechanical gripper, an electromagnetic actuator and a force feedback controller. The mechanical gripper is operable to be actuated to one of a plurality of gripping poses for gripping an object. The electromagnetic actuator includes a MRE, wherein the MRE is operable to be transitioned between a plurality of shapes dependent upon a variable strength of a magnetic field applied to the MRE, and wherein each shape of the MRE actuates the mechanical gripper to one of the gripping poses. The force feedback controller is operable to control the strength of the magnetic field applied to the MRE based on an estimation of a gripping force of the mechanical gripper and on a sensing of a load force of the object responsive to the gripping force of the mechanical gripper.

A third form of the present invention is a method of controlling the aforementioned force feedback gripper device. The method involves an application of a magnetic field to the MRE, wherein the MRE is transitioned between the plurality of shapes dependent upon a variable strength of a magnetic field, and wherein each shape of the MRE actuates the mechanical gripper to one of the plurality of gripping poses for gripping the object. The method further involves a control of the variable strength of the magnetic field applied to the MRE based on an estimation of a gripping force of the mechanical gripper and on a sensing of a load force of the object responsive to the gripping force of the mechanical gripper.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
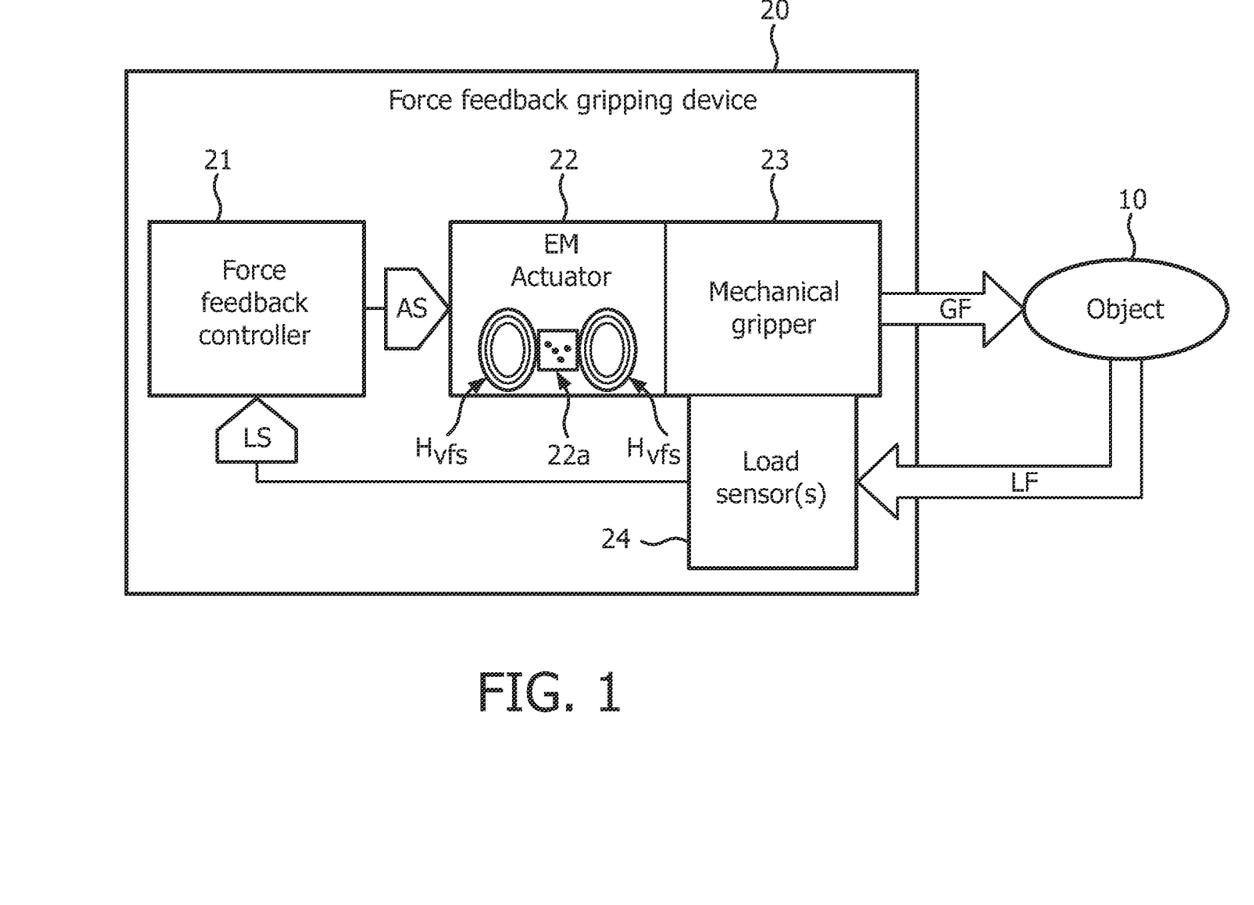
FIG. 1 illustrates an exemplary embodiment of a force feedback gripping device in accordance with the present invention.

Referring to FIG. 1, a force feedback gripping device 20 of the present invention employs a force feedback controller 21, an electromagnetic actuator 22, a mechanical gripper 23 and a load sensor 24 for gripping an object 10, particularly an anatomical object (e.g., an organ, a blood vessel, a foreign body, etc.). For purposes of the present invention, the term "gripping" is broadly defined herein as any forceful contact of device 20 upon object 10 including, but not limited to, device 20 gripping, grasping, clamping, squeezing, clutching and/or holding object 10.

In general operation, force feedback controller 21 communicates an actuation signal AS to electromagnetic actuator 22 to control a generation by electromagnetic actuator 22 of a magnetic field $H_{vfs}$ of variable strength that is applied to a magnetorheological elastomer ("MRE") 22a. The strength of magnetic field $H_{vfs}$ determines a two-dimensional ("2D") or three-dimensional ("3D") shape of MRE 22a, and any variation in the strength of magnetic field $H_{vfs}$ alters a shape of MRE 22a between a baseline shape associated with a minimal strength of magnetic field $H_{vfs}$ (e.g., zero magnetic flux density B of MRE 22a) and a fully actuated shape associated with a maximal strength of magnetic field $H_{vfs}$ (e.g., saturated magnetic flux density B of MRE 22a).

In practice, a "shape" of MRE 22a broadly encompasses any general shape (e.g., circles, spheres, polygons, prisms, cylinders, cones, etc.), and a "plurality of shapes" of MRE 22a broadly encompasses (1) variances in one or more dimensions of the same general shape, and/or (2) a transition between two (2) general shapes. For example, MRE 22a may have a general prism shape that is in cubic form when a minimal strength of magnetic field $H_{vfs}$ is applied to MRE 22a and that is elongated to a rectangular form when a maximal strength of magnetic field $H_{vfs}$ is applied to MRE 22a, or vice-versa. By further example, MRE 22 may have a cylinder shape when a minimal strength of magnetic field $H_{vfs}$ is applied to MRE 22a that transitions to a cone shape as the maximal strength of magnetic field $H_{vfs}$ is applied to MRE 22a, or vice-versa.

Additionally, the use of the terms "minimal" and "maximum" for the strength magnetic field $H_{vfs}$ is used for relative value purposes and not absolute minimum and maximum magnetic field strength values that are capable of being generated by electromagnetic actuator 22. Thus, in practice, the minimal strength of magnetic field $H_{vfs}$ may be a non-zero magnetic field and the maximal strength of magnetic field $H_{vfs}$ may or may not correspond to a saturated magnetic flux density B of MRE 22a.

Still referring to FIG. 1, mechanical gripper 23 is coupled to MRE 22a whereby each shape of MRE 22a actuates mechanical gripper 23 to one of a plurality of gripping poses between a minimal gripping pose corresponding to the baseline shape of MRE 22a and a maximum gripping pose corresponding to the fully actuated shape of MRE 22. As mechanical gripper 23 is actuated to grip object 10, object 10 experiences a load force LF dependent upon a gripping force GF of mechanical gripper 23, contact surfaces of mechanical gripper 23 and object 10, material properties of mechanical gripper 23 and object 10 (e.g., yield strength, fatigue strength, tensile strength, compressive strength, toughness, modulus of elasticity, ductility, etc.) and physical properties of mechanical gripper 23 and object 10 (e.g., mass, cross sectional area, etc.). Load sensor 24 communicates a load signal LS to force feedback controller 21 that is indicative of load force LF and in response thereto, force feedback controller 21 utilizes the sensing of load force LF via load signal LS and an estimation of gripping force GF to control the variable strength of magnetic field $H_{vsf}$ via actuation signal AS with the objective of mechanical gripper 23 securely gripping object 10 without inflicting any damage to object 10.

The following is a definitional description of force feedback controller 21, electromagnetic actuator 22, mechanical gripper 23 and load sensor 24.

For purposes of the present invention, force feedback controller 21 is broadly defined herein as any data processing structure configured for controlling the variable strength of magnetic field $V_{vsf}$ via actuation signal AS based on an estimation of gripping force GF and on a sensing of load force LF via load signal LS. Examples of force feedback controller 21 include, but are not limited to, a microprocessor (e.g., a digital signal processor), a microcontroller, dedicated hardware/firmware, programmable hardware and reprogrammable firmware. In practice, actuation signal AS may have any electrical signal form (e.g., voltage or current, DC or AC, etc.) and may be communicated to electromagnetic actuator 22 by any form of electric signal transmission (e.g., electrical or optical, wired or wireless, etc.). Also in practice, force feedback controller 21 may be integrated with magnetic actuator 22 and/or mechanical gripper 23, or physically remote from magnetic actuator 22 and mechanical gripper 23.

For purposes of the present invention, electromagnetic actuator 22 is broadly defined herein as any electromagnetic structure employing any type of elastomer having magnetorheological fluid/particles whereby elastic properties of the elastomer are controllable by a locally generated variable strength magnetic field $H_{vrf}$. In practice, MRE 22a may have any material composition suitable for desired application(s) of device 20. In one embodiment, MRE 22a is composed of ferromagnetic particles embedded in a polymer matrix. For example, the ferromagnetic particles are 3-5 µm pure iron embedded in a rubber matrix (e.g., silicone rubber).

Also in practice, MRE 22a may have any alignment relative to the locally generated variable magnetic field $H_{vfs}$. Furthermore, MRE 22a may be directly coupled to mechanical gripper 23 or electromagnetic actuator 22 may additionally include component(s) coupling MRE 22a to mechanical gripper 23 (e.g., a spring, a lever, etc.).

For purposes of the present invention, mechanical gripper 23 is broadly defined herein as any mechanical structure employing one or more components for gripping object(s) of any type in response to physical forces being applied to the component(s) from MRE 22a. In practice, the structural configuration of mechanical gripper 23 is dependent upon particular industry(ies) having use of mechanical gripper 23 (e.g., medical, biomedical, manufacturing, semiconductor, etc.). For the medical industry, exemplary uses of mechanical gripper 23 include, but are not limited to, gripping of tissue in conventional surgery (e.g. laparoscopy) and microsurgery (e.g. eye surgery), gripping of small particles (e.g., blood clots or foreign bodies) or micro-gripping. Also, in practice, mechanical gripper 23 may be an end effector of a robotic system.

For purposes of the present invention, load sensor 24 is broadly defined herein as any sensor structure configured for converting a load force acting on the structure into any type of electronic signal indicative of a magnitude of the load force. Examples of load sensor 24 include, but are not limited to, load cell sensors, force sensors, torque sensors and pressure sensors. In practice, load signal LS may have any electrical signal form (e.g., voltage or current, DC or AC, etc.) and may be communicated to force feedback controller 21 by any form of electric signal transmission (e.g., electrical or optical, wired or wireless, etc.). Also in practice, one or more load sensors 24 may be employed and each load sensor 24 may be coupled to mechanical gripper 23 adjoined or adjacent to contact surfaces of mechanical gripper 23 in a manner than facilitates a sensing of the load force upon object 10.

The following is a description of exemplary embodiments of force feedback controller 21, electromagnetic actuator 22 and mechanical gripper 23 as shown in FIGS. 2-9 to facilitate further understanding of the present invention.

Figure 2A:
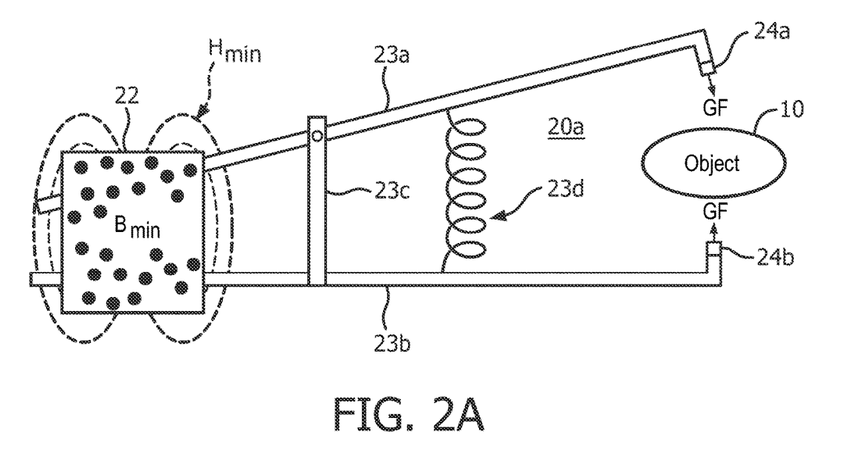
FIGS. 2A and 2B illustrate a first exemplary embodiment of a MRE gripping device in accordance with the present invention shown in an open state and a closed state, respectively.
Figure 2B:
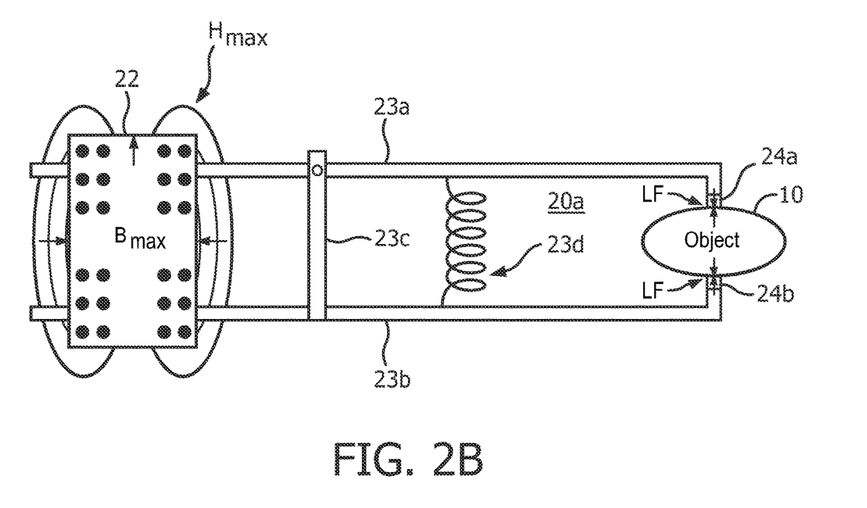

One exemplary embodiment 20a of device 20 is shown in FIG. 2A in an open state and in FIG. 2B in a closed state. Mechanical gripper 23 of device 20a employs a gripper frame having a gripper arm 23a pivotally connected to a lever 23c and a gripper arm 23b fixedly connected to lever 23c. The gripper frame further has a spring 23d for biasing mechanical gripper 23 to the open state as shown in FIG. 2A.

A load sensor 24a of device 20a is adjoined to a distal contact surface of gripper arm 23a, and a load sensor 24b of device 20a is adjoined to a distal contact surface of gripper arm 23b. Alternatively, load sensors 24a and 24b may be adjacent distal contact surfaces of respective gripper arms 23a and 23b.

A proximal end of gripper arm 23a and a proximal end of gripper arm 23b are connected to electromagnetic actuator 22. This establishes a parallel alignment of electromagnetic actuator 22 and spring 23d relative to lever 23c. MRE 22a of electromagnetic actuator 22 (symbolically shown by the particle dots) has a shape memory property created by a molding of MRE 22a in a baseline shape shown in FIG. 2A (e.g., a cubic prism shape).

As shown in FIG. 2A, MRE 22a maintains the baseline shape upon an application of a minimal field strength $H_{min}$ of magnetic field $H_{vfs}$ (e.g., a zero magnetic field), and gripper arms 23a and 23b are biased by spring 23d to a minimal gripping pose representative of an open state of device 20a. The baseline shape of MRE 22a corresponds to a minimum stiffness of MRE 22a in view of a minimal magnetic flux density $B_{min}$ and as such a minimal gripping force GF of gripper arms 23a and 23b.

To close device 20a upon object 10, force feedback controller 21 (not shown) controls an increase in the strength of magnetic field $H_{vfs}$ toward a maximal strength $H_{max}$ as shown in FIG. 2B resulting in a parallel expansion of MRE 22a from the baseline shape to a fully actuated shape (e.g., a rectangular prism shape) associated with the maximal strength $H_{max}$ of magnetic field $H_{vfs}$ (e.g., a saturated magnetic field). More particularly, as the strength of magnetic field $H_{vfs}$ is increased, the stiffness of MRE 22a increases responsive to an increasing magnetic flux density B thereby increasing the gripping force GF of gripper arms 23a and 23b to a maximal level corresponding to the fully actuated shape of MRE 22a.

Load sensors 24a and 24b communicate load signals to force feedback controller 21 (not shown) whereby force feedback controller 21 controls the increase in the strength of magnetic field $H_{vfs}$ towards the maximal strength $H_{max}$ with the objective of securely gripping object 10 without inflicting any damage to object 10. As such, force feedback controller 21 may increase the strength of magnetic field $H_{vfs}$ to a lower strength than maximal strength $H_{max}$ if the load signals LS in conjunction with an estimation of the increasing gripping force GF indicate object 10 may experience damage if the strength of magnetic field $H_{vfs}$ is further increased toward the maximal strength $H_{max}$.

Figure 3A:
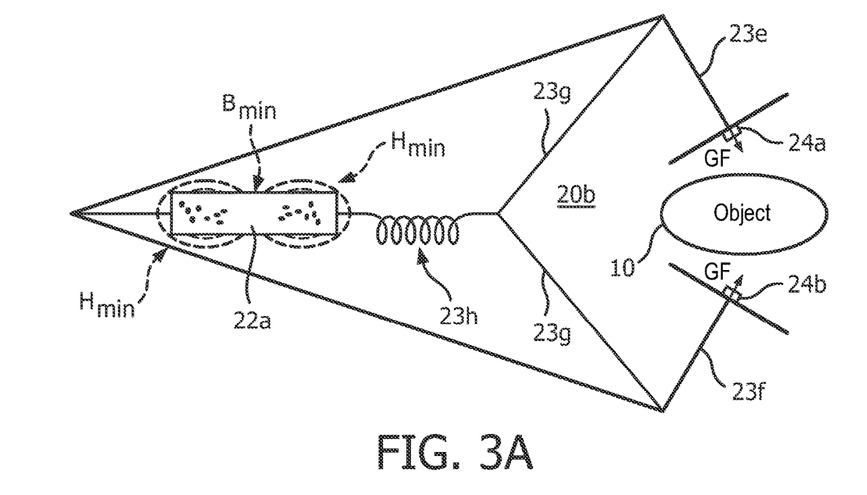
FIGS. 3A and 3B illustrate a second exemplary embodiment of a MRE gripping device in accordance with the present invention shown in an open state and a closed state, respectively.
Figure 3B:
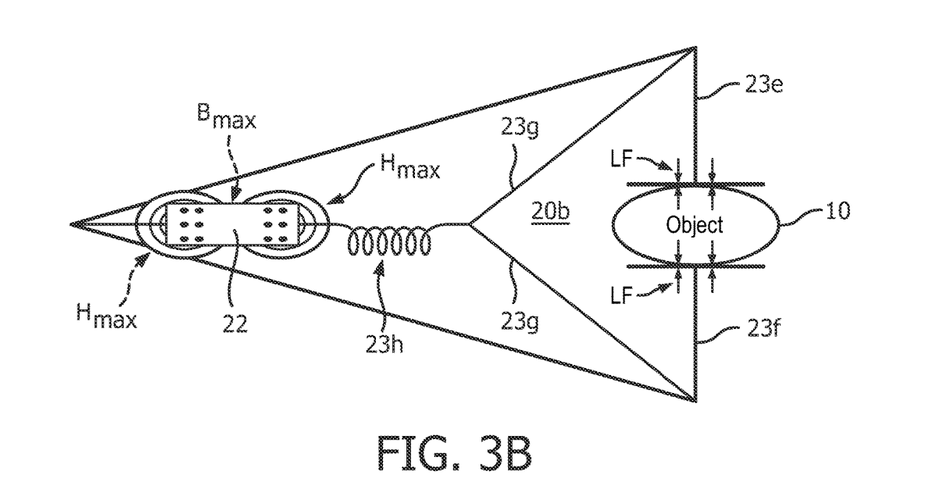

Another exemplary embodiment 20b of device 20 is shown in FIG. 3A in an open state and in FIG. 3B in a closed state. Mechanical gripper 23 of device 20b employs a gripper frame having a gripper arm 23e and a gripper arm 23f both pivotally connected to a lever 23g, and a spring 23h connected lever 23g and to a distal side of magnetic actuator 22.

A load sensor 24a of device 20b is adjoined to a distal contact surface of gripper arm 23e, and a load sensor 24b of device 20b is coupled to gripper arm 23f adjoined to a distal contact surface of gripper arm 23f. Alternatively, load sensors 24a and 24b may be adjacent distal contact surfaces of respective gripper arms 23e and 23f A proximal end of gripper arms 23e and 23f are pivotally coupled to a proximal side of electromagnetic actuator 22. This establishes a series alignment of electromagnetic actuator 22 and spring 23g relative to gripper arms 23e and 23f For this embodiment, MRE 22a of electromagnetic actuator 22 (symbolically shown by the particle dots) has a shape memory property created by a molding of MRE 22a in a baseline shape shown in FIG. 3A (e.g., a rectangular prism shape).

As shown in FIG. 3A, MRE 22a maintains the baseline shape upon an application a minimal field strength $H_{min}$ of magnetic field $H_{vfs}$ (e.g., a zero magnetic field), and gripper arms 23e and 23f are biased by spring 23d to a minimal gripping pose representative of an open state of device 20b. The baseline shape of MRE 22a corresponds to a minimum stiffness of MRE 22a in view of a minimal magnetic flux density $B_{min}$ and as such a minimal gripping force GF of gripper arms 23e and 23f.

To close device 20b upon object 10, force feedback controller 21 (not shown) controls an increase in the strength of magnetic field $H_{vfs}$ toward a maximal strength $H_{max}$ as shown in FIG. 3B resulting in a series compression of MRE 22a from the baseline shape to a fully actuated shape (e.g., a cubic prism shape) associated with the maximal strength $H_{max}$ of magnetic field $H_{vfs}$ (e.g., a saturated magnetic field). More particularly, as the strength of magnetic field $H_{vfs}$ is increased, the stiffness of MRE 22a increases responsive to an increasing magnetic flux density B thereby increasing the gripping force GF of gripper arms 23e and 23f to a maximal level corresponding to the fully actuated shape of MRE 22a.

Load sensors 24a and 24b communicate load signals to force feedback controller 21 (not shown) whereby force feedback controller 21 controls the increase in the strength of magnetic field $H_{vfs}$ toward a maximal strength $H_{max}$ with the objective of securely gripping object 10 without inflicting any damage to object 10. As such, force feedback controller 21 may increase the strength of magnetic field $H_{vfs}$ to a lower strength than maximal strength $H_{max}$ if the load signals LS in conjunction with an estimation of the increasing gripping force GF indicate object 10 may experience damage if the strength of magnetic field $H_{vfs}$ is further increased to a maximal strength $H_{max}$.

Figure 4:
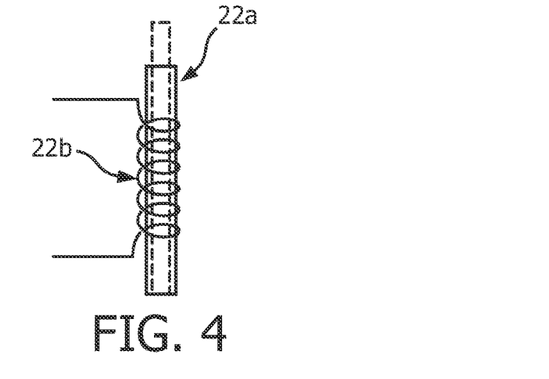
FIG. 4 illustrates a first exemplary embodiment of a MRE electromagnet in accordance with the present invention.
Figure 5:
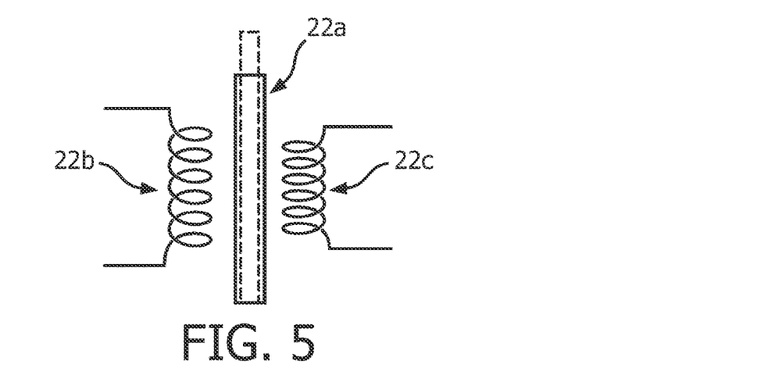
FIG. 5 illustrates a second exemplary embodiment of a MRE electromagnet in accordance with the present invention.
Figure 6:
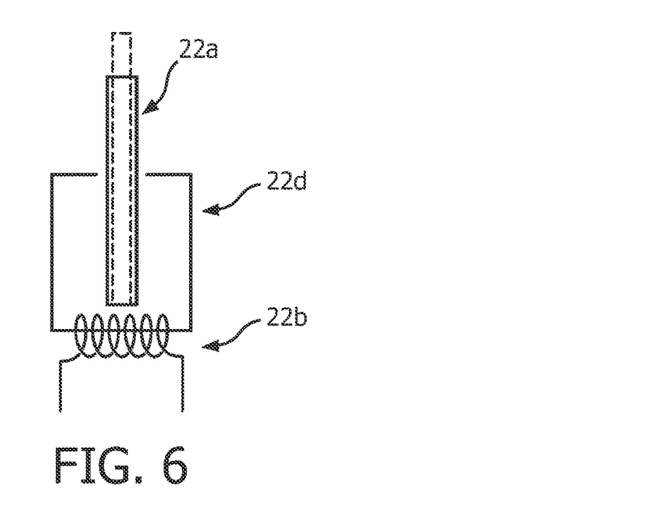
FIG. 6 illustrates a third exemplary embodiment of a MRE electromagnet in accordance with the present invention.

For device 20a (FIG. 2), device 20b (FIG. 3) and any other embodiment of device 20 of the present invention, FIGS. 4-6 illustrate various embodiments of an electromagnet of electromagnetic actuator 22. Specifically, FIG. 4 shows a coil 22b wrapped around a cylindrical MRE 22a whereby a magnetic field (not shown) generated by coil 22b is aligned along a longitudinal axis of MRE 22a. Coil 22b generates the magnetic field responsive to current flowing through coil 22b whereby MRE 22a may be elongated as shown by the dashed lines along the longitudinal axis of MRE 22a in dependence upon the strength of the magnetic field.

FIG. 5 shows a serial bipolar arrangement coil 22b and a coil 22c relative to cylindrical MRE 22a whereby magnetic fields (not shown) generated by coils 22b and 22c are parallel to a longitudinal axis of MRE 22a. Coils 22b and 22c generate the magnetic fields when current flows through coils 22b and 22c whereby MRE 22a may be elongated as shown by the dashed lines along the longitudinal axis of MRE 22a in dependence upon the strength of the magnetic field.

FIG. 6 shows coil 22b wrapped around an iron core 22d providing an air gap around cylindrical MRE 22a whereby a magnetic field (not shown) generated by coil 22b magnetizes iron core 22d, which in turn magnetizes MRE 22a. Coil 22b generates the magnetic field (not shown) responsive to current flowing through coil 22b whereby MRE 22a may be elongated as shown by the dashed lines along the longitudinal axis of MRE 22a in dependence upon the strength of the magnetic field.

For FIGS. 4-6, the cylindrical shape of MRE 22a as shown may serve as the baseline shape or the fully actuated shape.

Figure 7:
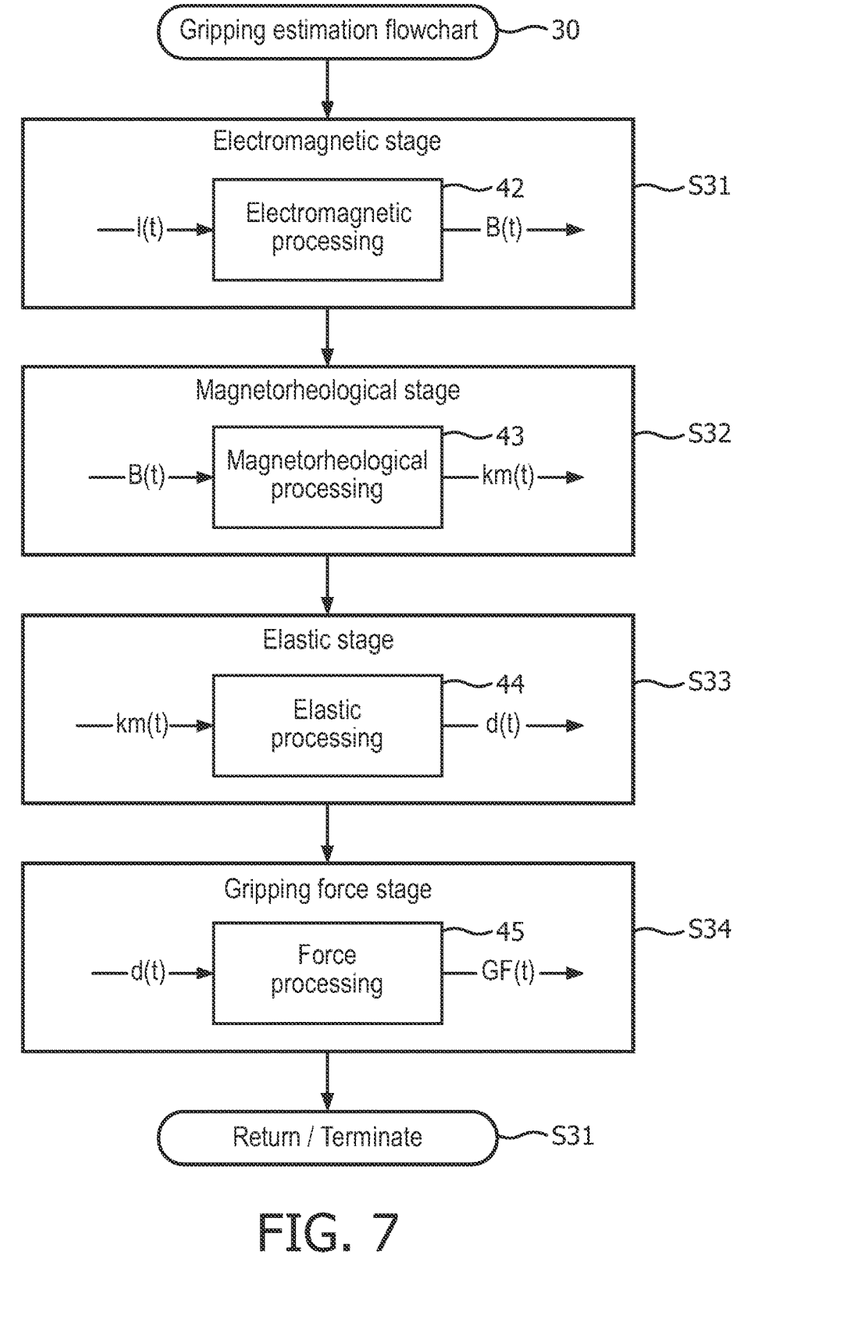
FIG. 7 illustrates a flowchart representative of an exemplary embodiment of a gripping force estimation method in accordance with the present invention.

For device 20a (FIG. 2), device 20b (FIG. 3) and any other embodiment of device 20 of the present invention, FIG. 7 illustrates a flowchart representative of gripping force estimation method performed by force feedback controller 21. Specifically, gripping force GF of mechanical gripper 23 is a function of a stiffness of MRE 22a, which is controlled by the magnetic flux density of MRE 22a. In practice, gripping force GF of mechanical gripper 23 may increase as the stiffness of MRE 22a increases as shown in FIGS. 2 and 3, or decrease as the stiffness of MRE 22a increases in dependence upon a particular coupling of electromagnetic actuator 22 to mechanical gripper 23. Force feedback controller 21 therefore utilizes the elastic modulus of MRE 22a as a basis for estimating the gripping force GF of mechanical gripper 23.

Referring to FIG. 7, a stage S31 of flowchart 30 encompasses an electromagnetic processing 42 of a current signal I(t) for an electromagnet to yield a magnetic flux density B(t). In one embodiment of stage S31, electromagnetic processing 42 includes an execution of the following equation [1].

$$B(t) = \mu_m n I(t) \quad [1]$$

where $\mu_m$ is magnetic permeability of MRE 22a and n is density of wire turns in a coil of the electromagnet.

Figure 9:
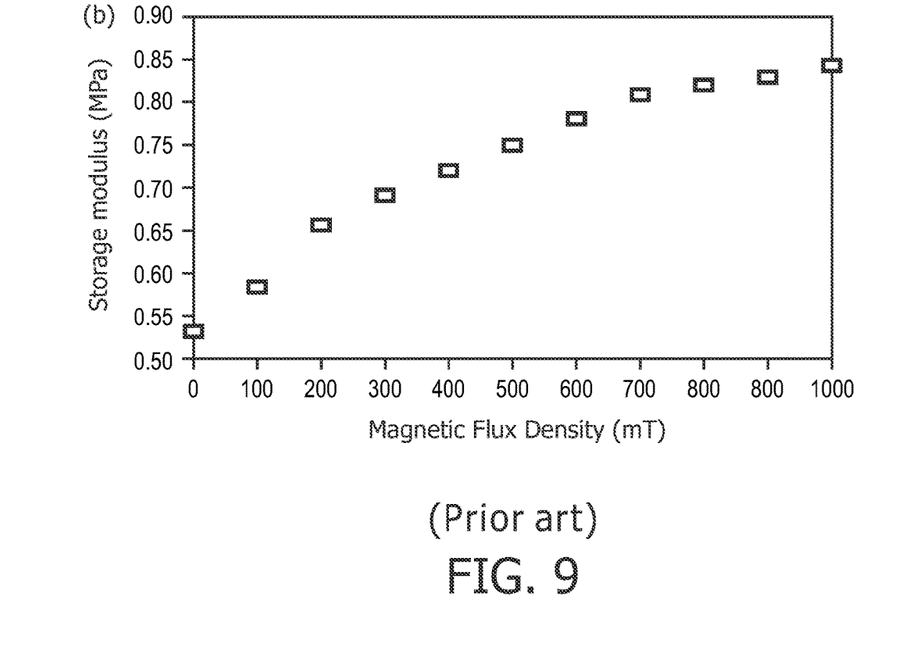
FIG. 9 illustrates a known characterization curve of a MRE.

A stage S32 of flowchart 30 encompasses a magnetorheological processing 43 of magnetic flux density B(t) to yield an elastic constant km(t) of MRE 22a. In one embodiment of stage S32, magnetorheological processing 43 involves an experimental determination of elastic constant $k_m(B)$ as known in the art. For example, FIG. 9 shows a characteristics curve determined by experiment of a particular designed MRE describing a relationship between elastic modulus (E) and magnetic flux density E=f(B). For this curve, the magnetorheological processing 43 includes an execution of the following equation [2]:

$$k_m(t) = (EB(t)A)/L \quad [2]$$

where A is cross sectional area of MRE 22a and L is a length of MRE 22a when is not compressed.

A stage S33 of flowchart 30 encompasses an elastic processing 44 of elastic constant km(t) to yield a displacement d(t) of gripper arms from the open state. In one embodiment of stage S33, elastic processing 44 of elastic constant km(t) may be based on physical forces on electromagnetic actuator 22, the spring and a geometry of mechanical gripper 24. For simplicity, this embodiment assumes (1) physical forces on mechanical gripper 24 are negligible compared to forces in biasing component and on MRE 22a, (2) MRE 22a and the spring are not changing their shape if fully compressed, (3) a length of the spring in resting position is exactly a distance between the contact surfaces of the gripper arms when parallel and (4) a length of MRE 22a in resting position is shorter than a distance between the contact surfaces of the gripper arms when parallel. Thus, further assuming that two forces applied on the lever are a force $F_S$ on the spring and a force $F_m$ on MRE 22a, equalizing the moments and using elastic force as $F = -k(t) \ast \Delta x$, where $\Delta x$ is an elongation of MRE 22a, the forces are in accordance with the following equations [3] and [4]:

$$F_S \cdot l_S = F_M \cdot l_M \quad [3]$$

$$k_S \cdot l_S \cdot \Delta x_S = k_M \cdot l_M \cdot \Delta x_M \quad [4]$$

Further, using trigonometric relations, relationship between vertical displacements from the fulcrum point in accordance with the following equation [5]:

$$\Delta x'_S = \frac{l_S}{l_M} \cdot \Delta x'_M \quad [5]$$

Note that displacement from the fulcrum and elastic displacement are not always equal. Under the initial assumptions, $\Delta x'_S = \Delta x_S$ and $\Delta x_M = \Delta x'_M + \Delta x_0$ where $\Delta x_0$ is additional extension of the MRE 22a with respect to the fulcrum point. Combining force equation and geometric equation yields the following equation [6]:

$$\Delta x'_M = \left(1 - \frac{k_S \cdot l_S^2}{k_M \cdot l_M^2}\right) \Delta x_0 \quad [6]$$

Total opening of the gripper jaws is therefore in accordance with the following equation [7]:

$$d = h + \frac{l}{l_M}\left(1 - \frac{k_S \cdot l_S^2}{k_M \cdot l_M^2}\right) \Delta x_0 \quad [7]$$

Equation (7) describes the elastic component of the control system. Elastic constant of the spring $k_S$ is constant and depends on the design and material of the spring. Lengths l, $l_M$, $l_S$ and height h are constant and depend on design of the gripper. $\Delta x_0$ is also constant. Thus, the opening of the gripper jaws is proportional to $k_m(t)$ with a transfer function is described by magnetorheological component.

A stage S34 of flowchart 30 encompasses a force processing 45 of displacement d(t) to yield a gripping force GF(t). In one embodiment of stage S34, gripping force GF(t) may be assumed to be linear: $F = -k_o \Delta x_o$, where $k_o$ is an elastic constant of the object and $\Delta x_o$ is deformation of the object. As deformation of the object is directly proportional to jaw opening d(t), it can be assumed that the gripping force GF(t) is also directly proportional to jaw opening d(t) for any given gripper task.

Figure 8:
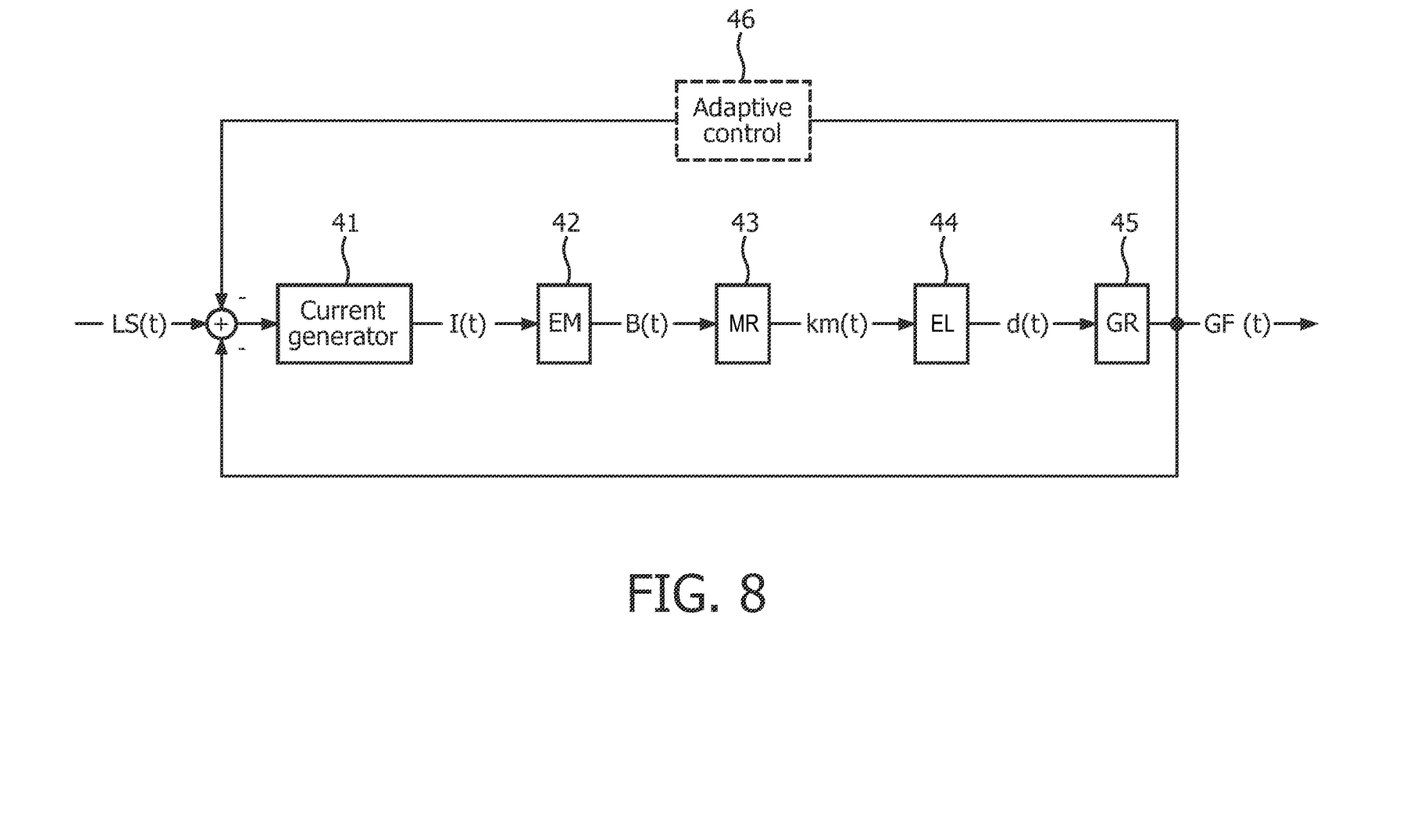
FIG. 8 illustrates an exemplary embodiment of a force feedback control scheme in accordance with the present invention.

Referring to FIG. 8, force feedback control 21 executes software and/or firmware having instructions for implementing a force feedback control scheme incorporating gripper force estimation method 30 shown in FIG. 7. For this control scheme, a current generator 41 processes a differential of a load force LF(t) and gripping force GF(t) to yield current I(t) for the coil of the electromagnet. In one embodiment, current I(t) is a function of the differential of load force LF(t) and gripping force GF(t) as shown in the following Table 1:

| Load Force/Gripping Force Differential | Current |
|---|---|
| <0 | Increase |
| =0 | Maintain |
| >0 | Decrease |

In practice, an offset X may be subtracted or added to the Load Force/Gripping Force Differential of Table 1 in dependence upon the particular object 10 being gripped by device 20.

Also in practice, since the actual force component of the transfer function is not known, an adaptable control 46 as shown in FIG. 8 may be applied. In one embodiment, adaptable control 46 may be realized as adaptive gain component as shown (unknown proportional contest) and force feedback controller 31 may be generalized proportional-integral-derivative ("PID") controller. This embodiment can be used to provide real-time control of the gripping force GF(t).

Referring to FIGS. 1-9, those having ordinary skill in the art will appreciate numerous benefits of the present invention including, but not limited to, a force feedback gripping device securely gripping an object via control of a MRE for minimizing, if not preventing, an infliction of damage to the object by the device.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A MRE gripping device, comprising:
a mechanical gripper operable to be actuated to one of a plurality of gripping poses for gripping an object; and
an electromagnetic actuator structurally segregated from the mechanical gripper and including a magnetorheological elastomer,
wherein the magnetorheological elastomer is operable to be transitioned between a plurality of shapes dependent upon a variable strength of a magnetic field applied to the magnetorheological elastomer,
wherein each shape of the magnetorheological elastomer actuates the mechanical gripper to one of the gripping poses, and
wherein one of:
the electromagnetic actuator further includes a bipolar arrangement of coils relative to the magnetorheological elastomer, or
the electromagnetic actuator further includes an iron core and a coil wrapped around the iron core, and the magnetorheological elastomer is positioned within an air gap of the iron core.

2. The MRE gripping device of claim 1, wherein the mechanical gripper includes at least one load sensor operable to sense a load force of the object responsive to the gripping force of the mechanical gripper.

3. The MRE gripping device of claim 1,
wherein the mechanical gripper includes a plurality of gripper arms actuatable between a minimum gripping pose and a maximum gripping pose; and
wherein the electromagnetic actuator is connected to the plurality of gripper arms.

4. The MRE gripping device of claim 1,
wherein the mechanical gripper includes a plurality of gripper arms actuatable between a minimum gripping pose and a maximum gripping pose; and
wherein the electromagnetic actuator is coupled to the plurality of gripper arms.

5. A force feedback gripping device, comprising:
a mechanical gripper operable to be actuated to one of a plurality of gripping poses for gripping an object;
an electromagnetic actuator including a magnetorheological elastomer,
wherein the magnetorheological elastomer is operable to be transitioned between a plurality of shapes dependent upon a variable strength of a magnetic field applied to the magnetorheological elastomer, and
wherein each shape of the magnetorheological elastomer actuates the mechanical gripper to one of the gripping poses; and
a force feedback controller operable to control the variable strength of the magnetic field applied to the magnetorheological elastomer based on an estimation of a gripping force of the mechanical gripper and on a sensing of a load force of the object responsive to the gripping force of the mechanical gripper.

6. The force feedback gripping device of claim 5, wherein the mechanical gripper includes at least one load sensor operable to sense the load force of the object responsive to the gripping force of the mechanical gripper.

7. The force feedback gripping device of claim 5, wherein the electromagnetic actuator further includes a coil wrapped around the magnetorheological elastomer.

8. The force feedback gripping device of claim 5, wherein the electromagnetic actuator further includes a bipolar arrangement of coils relative to the magnetorheological elastomer.

9. The force feedback gripping device of claim 5,
wherein electromagnetic actuator further includes an iron core and a coil wrapped around the iron core, and
wherein the magnetorheological elastomer is positioned within an air gap of the iron core.

10. The force feedback gripping device of claim 5, wherein the variable strength of the magnetic field applied to the magnetorheological elastomer is derived as a function of a differential between the estimation of the gripping force of the mechanical gripper and the sensing of the load force of the object responsive to the gripping force of the mechanical gripper.

11. The force feedback gripping device of claim 5, wherein the gripping force of the mechanical gripper is a function of a material stiffness of the magnetorheological elastomer responsive to the magnetic field.

12. The force feedback gripping device of claim 5,
wherein the mechanical gripper includes a plurality of gripper arms actuatable between a minimum gripping pose and a maximum gripping pose; and
wherein the electromagnetic actuator is connected to the plurality of gripper arms.

13. The force feedback gripping device of claim 5,
wherein the mechanical gripper includes a plurality of gripper arms actuatable between a minimum gripping pose and a maximum gripping pose; and
wherein the electromagnetic actuator is coupled to the plurality of gripper arms.

14. A method of controlling a force feedback gripper device including a mechanical gripper and an electromagnetic actuator including a magnetorheological elastomer, the method comprising:
applying a magnetic field to the magnetorheological elastomer,
wherein the magnetorheological elastomer is transitioned between a plurality of shapes dependent upon a variable strength of a magnetic field, and
wherein each shape of the magnetorheological elastomer actuates the mechanical gripper to one of a plurality of gripping poses for gripping the object; and
controlling the variable strength of the magnetic field applied to the magnetorheological elastomer based on an estimation of a gripping force of the mechanical gripper and a sensing of a load force of the object responsive to the gripping force of the mechanical gripper.

15. The method of claim 14, wherein the variable strength of the magnetic field applied to the magnetorheological elastomer is derived as a function of a differential between the estimation of the gripping force of the mechanical gripper and the sensing of the load force of the object responsive to the gripping force of the mechanical gripper.

16. The method of claim 15, wherein the gripping force of the mechanical gripper is a function of a material stiffness of the magnetorheological elastomer responsive to the magnetic field.

17. The method of claim 14,
wherein the mechanical gripper includes a plurality of gripper arms actuatable between a minimum gripping pose and a maximum gripping pose.

* * * * *